United States Patent
Herold et al.

(10) Patent No.: US 9,078,943 B2
(45) Date of Patent: Jul. 14, 2015

(54) HYDROGEN PEROXIDE SUPPLY FOR STERILIZATION OF A CONTAINER, INCLUDING A BYPASS ARRANGEMENT FOR RECIRCULATION OF HYDROGEN PEROXIDE

(75) Inventors: Thomas Herold, Ahrensburg (DE); Roland Topf, Hamburg (DE)

(73) Assignee: KHS GmbH, Dortmund (DE)

( * ) Notice: Subject to any disclaimer, the term of this patent is extended or adjusted under 35 U.S.C. 154(b) by 772 days.

(21) Appl. No.: 12/707,372

(22) Filed: Feb. 17, 2010

(65) Prior Publication Data
US 2010/0205907 A1 Aug. 19, 2010

Related U.S. Application Data

(63) Continuation-in-part of application No. PCT/EP2008/005828, filed on Jul. 17, 2008.

(30) Foreign Application Priority Data

Aug. 17, 2007 (DE) .......................... 10 2007 039 010

(51) Int. Cl.
*A61L 2/20* (2006.01)
*B65B 55/10* (2006.01)
*A61L 2/24* (2006.01)
*G05D 7/06* (2006.01)

(52) U.S. Cl.
CPC . *A61L 2/208* (2013.01); *A61L 2/24* (2013.01); *B65B 55/10* (2013.01); *G05D 7/0635* (2013.01); *A61L 2202/18* (2013.01); *A61L 2202/23* (2013.01)

(58) Field of Classification Search
CPC ...... B65B 55/18; B65B 55/10; B65B 55/103; B65B 55/106; A61L 2/208; A61L 2209/211; A61L 2202/18; A61L 2202/23; A61L 2/186

USPC ................ 53/426, 432, 425, 167; 422/31, 40, 422/28–29, 292–304
See application file for complete search history.

(56) References Cited

U.S. PATENT DOCUMENTS 3,750,367 A * 8/1973 Barker et al. .................... 53/167
4,511,538 A * 4/1985 Buchner et al. ............... 422/303
(Continued)

FOREIGN PATENT DOCUMENTS

DE 36 37 798 A1 5/1988
DE 3728595 A1 * 3/1989 .............. B65B 55/10
(Continued)

OTHER PUBLICATIONS

EPO machine translation of DE4036950, retrieved from espacenet.com on Sep. 3, 2014, 5 pages.*
(Continued)

*Primary Examiner* — Stephen F Gerrity
(74) *Attorney, Agent, or Firm* — Nils H. Ljungman & Associates

(57) ABSTRACT

A hydrogen peroxide ($H_2O_2$) supply arrangement which has a storage container for the $H_2O_2$ and metering valves designed to meter doses of $H_2O_2$ to a plurality of article sterilization devices. The $H_2O_2$ supply arrangement also has a line arrangement which connects the storage container to the metering valves. The line arrangement is designed so as to conduct $H_2O_2$ to the metering valves, but also to cycle $H_2O_2$ not metered or dosed out by the metering valves back into the $H_2O_2$ storage container in a cyclical manner. The $H_2O_2$ supply arrangement is designed in this manner to minimize decomposition of the $H_2O_2$, and thus minimize waste and improve accuracy of the metered doses.

17 Claims, 6 Drawing Sheets

(56) References Cited

U.S. PATENT DOCUMENTS

| | | | |
|---|---|---|---|
| 4,936,486 A * | 6/1990 | Kummerer | 222/42 |
| 5,007,232 A * | 4/1991 | Caudill | 53/426 |
| 5,527,507 A | 6/1996 | Childers et al. | |
| 5,556,607 A * | 9/1996 | Childers et al. | 422/300 |
| 5,906,794 A * | 5/1999 | Childers | 422/28 |
| 6,537,491 B1 * | 3/2003 | Wang et al. | 422/28 |
| 2003/0068251 A1 * | 4/2003 | Smith et al. | 422/28 |

FOREIGN PATENT DOCUMENTS

| | | |
|---|---|---|
| DE | 38 19 419 A1 | 12/1989 |
| DE | 40 36 950 A1 | 5/1992 |
| DE | 199 56 186 A1 | 5/2001 |
| EP | 0 353 486 A1 | 2/1990 |
| WO | WO 2006/128884 A2 | 12/2006 |

OTHER PUBLICATIONS

International Search Report PCT/EP2008/005828 and English translation thereof, mailed Jun. 24, 2009, 6 pages.

German Search Report 10 2007 039 010.8-41, mailed Jun. 12, 2008, 4 pages.

International Preliminary Report on Patentability PCT/EP2008/005828 and English translation thereof, mailed Jun. 24, 2009, 7 pages.

* cited by examiner

US 9,078,943 B2

HYDROGEN PEROXIDE SUPPLY FOR STERILIZATION OF A CONTAINER, INCLUDING A BYPASS ARRANGEMENT FOR RECIRCULATION OF HYDROGEN PEROXIDE

CONTINUING APPLICATION DATA

This application is a Continuation-In-Part application of International Patent Application No. PCT/EP2008/005828, filed on Jul. 17, 2008, which claims priority from Federal Republic of Germany Patent Application No. 10 2007 039 010.8, filed on Aug. 17, 2007. International Patent Application No. PCT/EP2008/005828 was pending as of the filing date of this application. The United States was an elected state in International Patent Application No. PCT/EP2008/005828.

BACKGROUND

1. Technical Field

The present application relates to a beverage bottle or container filling plant having a beverage bottle or container treatment arrangement and a method of operating a beverage bottle or container filling plant.

2. Background Information

Background information is for informational purposes only and does not necessarily admit that subsequently mentioned information and publications are prior art.

A beverage bottling plant for filling bottles with a liquid beverage filling material can possibly comprise a beverage filling machine, which is often a rotary filling machine, with a plurality of beverage filling positions, each beverage filling position having a beverage filling device for filling bottles with liquid beverage filling material. The filling devices may have an apparatus designed to introduce a predetermined volume of liquid beverage filling material into the interior of bottles to a substantially predetermined level of liquid beverage filling material.

Some beverage bottling plants may possibly comprise filling arrangements that receive a liquid beverage material from a toroidal or annular vessel, in which a supply of liquid beverage material is stored under pressure by a gas. The toroidal vessel may also be connected to at least one external reservoir or supply of liquid beverage material by a conduit or supply line. In some circumstances it may even be possible that a beverage bottling plant has two external supply reservoirs, each of which may be configured to store either the same liquid beverage product or different products. These reservoirs could possibly be connected to the toroidal or annular vessel by corresponding supply lines, conduits, or other arrangements. It is also possible that the external supply reservoirs could be in the form of simple storage tanks, or in the form of liquid beverage product mixers.

A wide variety of types of filling elements are used in filling machines in beverage bottling or container filling plants for dispensing a liquid product into bottles, cans or similar containers, including but not limited to filling processes that are carried out under counterpressure for the bottling of carbonated beverages. The apparatus designed to introduce a predetermined flow of liquid beverage filling material further comprises an apparatus that is designed to terminate the filling of the beverage bottles upon the liquid beverage filling material reaching the predetermined level in bottles. There may also be provided a conveyer arrangement that is designed to move bottles, for example, from an inspecting machine to the filling machine.

After a filling process has been completed, the filled beverage bottles are transported or conveyed to a closing machine, which is often a rotary closing machine. A revolving or rotary machine comprises a rotor, which revolves around a central, vertical machine axis. There may further be provided a conveyer arrangement configured to transfer filled bottles from the filling machine to the closing station. A transporting or conveying arrangement can utilize transport star wheels as well as linear conveyors. A closing machine closes bottles by applying a closure, such as a screw-top cap or a bottle cork, to a corresponding bottle mouth. Closed bottles are then usually conveyed to an information adding arrangement, wherein information, such as a product name or a manufacturer's information or logo, is applied to a bottle. A closing station and information adding arrangement may be connected by a corresponding conveyer arrangement. Bottles are then sorted and packaged for shipment out of the plant.

Many beverage bottling plants may also possibly comprise a rinsing arrangement or rinsing station to which new, non-return and/or even return bottles are fed, prior to being filled, by a conveyer arrangement, which can be a linear conveyor or a combination of a linear conveyor and a starwheel. Downstream of the rinsing arrangement or rinsing station, in the direction of travel, rinsed bottles are then transported to the beverage filling machine by a second conveyer arrangement that is formed, for example, by one or more starwheels that introduce bottles into the beverage filling machine.

It is a further possibility that a beverage bottling plant for filling bottles with a liquid beverage filling material can be controlled by a central control arrangement, which could be, for example, a computerized control system that monitors and controls the operation of the various stations and mechanisms of the beverage bottling plant.

In addition, beverage bottling plants may also comprise beverage bottle treatment arrangements or machines which treat the bottles with a treatment medium. An example of such a treatment arrangement could be a cleaning or sterilizing arrangement which cleans or sterilizes the bottles with either a treatment liquid, gas, or vapor, such as hydrogen peroxide.

The present application also relates to a metering and supplying system for the metered supplying of hydrogen peroxide to treatment heads of a device for hydrogen peroxide sterilization of packaging materials, said metering and supplying system including at least one storage container providing the hydrogen peroxide and a controllable connection between the at least one storage container and the respective treatment head. The present application also relates to a device for hydrogen peroxide sterilization of packaging materials, said device having a plurality of treatment heads for the introduction in each case of a heated hydrogen peroxide sterilization medium, comprising hydrogen peroxide and a vaporous and/or gaseous carrier, into the packaging materials to be sterilized and for the subsequent activating of the hydrogen peroxide sterilization medium, and having a metering and supplying system for the metered supplying of the hydrogen peroxide to the treatment heads.

The phrase "hydrogen peroxide sterilization" in terms of the present application means a sterilization of packaging materials by using hydrogen peroxide ($H_2O_2$). In this case, the hydrogen peroxide can be both in a sterilization medium or just the sole constituent of a sterilization medium. No difference is made between the two below and the term hydrogen peroxide sterilization medium is used below to include both.

"Packaging materials" in terms of the present application are, in one possible embodiment, bottles or similar containers, including KEGs, cans and tubes, but also other packaging, such as, for example, soft packaging or bags that have to be sterilized before the products, e.g. foodstuffs, drinks or tobacco, such as, for example beverages, or medicines, are introduced. The phrase "packaging materials" therefore covers virtually any type of containers, such as bottles, cans, boxes, packs, bags, pouches, kegs, etc., which can be used to contain a product, such as beverages, foods, medicines, and pharmaceuticals, for either storage or transport.

In some methods and devices for sterilizing packaging materials, the sterilizing may be done by using a hydrogen peroxide sterilization medium, which comprises hydrogen peroxide mixed with hot sterile air and is formed in treatment heads of the respective device for hydrogen peroxide sterilization. In the case of this method, with the hot hydrogen peroxide sterilization medium introduced into the packaging material via the respective treatment head, an hydrogen peroxide condensation film is formed by condensation on the inside surface of the cooler packaging material, said hydrogen peroxide condensation film then being activated in a subsequent activation phase by introducing a sterile hot gaseous and/or vaporous activating medium, for example by introducing hot sterile air, so that free oxygen radicals are created through the decomposition of hydrogen peroxide and they react with the germs and contaminants that are present for sterilization.

In order to carry out high quality hydrogen peroxide sterilization, i.e. at a high sterilization rate, in one possible embodiment also with a high degree of reliability and also in a manner that is reproducible and also verifiable, and at the same time to keep the consumption of hydrogen peroxide at low as possible, precise metering or substantially precise metering or metering of the addition of hydrogen peroxide is necessary and/or desired when accumulating the hydrogen peroxide sterilization medium at the treatment heads used.

Some methods include a central ring line. A plurality of dosing points are supplied via corresponding valves to sterilize the interior surface of containers. The ring line is thereby in hydrodynamic communication with a central storage container from which sterilizing agent is re-supplied as necessary and/or desired. A known problem with this arrangement is that many sterilizing agents give off a large amount of gas and/or tend to form bubbles. These effects are very disadvantageous for an exact fluid dosing, of the type that is necessary in the beverage industry, for example.

To control the degasification, some methods propose that a controlled check valve for the gas phase be provided in the return line to the pump which allows the discharge of the gas phase. Some methods involve transporting hydrogen peroxide from a central storage container via a ring line to the individual treatment points, whereby upstream of the dosing units metering devices are provided in which the fluid level is set to the quantity of fluid to be vaporized. These storage spaces are then blown out as necessary and/or desired. In systems with a great many dosing points this inclusion of the storage spaces and their blowing out leads to water hammers and increased bubble formation. Some methods propose the provision of a collecting container upstream of each dosing element, which is then emptied directly. This apparatus is very complex in terms of design and construction.

OBJECT OR OBJECTS

One possible object of this application is to describe a beverage bottle or container filling plant having a beverage bottle or container treatment arrangement and a method of operating a beverage bottle or container filling plant. Another possible object of the present application may be to provide a metering and supplying system, which enables optimum hydrogen peroxide metering with reproducible results. Another possible object of the present application may be to provide a metering and supplying system, which enables optimum hydrogen peroxide metering with reproducible results while avoiding a degassing or bubble formation in the supply lines.

SUMMARY

This object may be achieved with a metering and supplying system for the metered supplying of hydrogen peroxide to treatment heads of a device for hydrogen peroxide sterilization of packaging materials. The metering and supplying system may include at least one storage container providing the hydrogen peroxide and a controllable connection between the at least one storage container and the respective treatment head. The controllable connection is formed by at least one ring line, which, together with the at least one storage container, forms a cycle or circuit for the hydrogen peroxide. The respective treatment head is connected via at least one metering valve to the at least one ring line. This object may also be achieved with a device for hydrogen peroxide sterilization of packaging materials. The device may comprise a plurality of treatment heads for the introduction in each case of a heated hydrogen peroxide sterilization medium, comprising hydrogen peroxide and a vaporous and/or gaseous carrier, into the packaging materials to be sterilized and for the subsequent activating of the hydrogen peroxide sterilization medium. The device may also comprise a metering and supplying system for the metered supplying of the hydrogen peroxide to the treatment heads. The metering and supplying system is realized according to the present application.

Further developments, embodiments and application possibilities of the present application are produced from the subsequent description of exemplified embodiments and from the figures. In this case, all or substantially all described and/or graphically represented features are basically objects of the present application on their own or in arbitrary combination.

The above-discussed embodiments of the present invention will be described further herein below. When the word "invention" or "embodiment of the invention" is used in this specification, the word "invention" or "embodiment of the invention" includes "inventions" or "embodiments of the invention", that is the plural of "invention" or "embodiment of the invention". By stating "invention" or "embodiment of the invention", the Applicant does not in any way admit that the present application does not include more than one patentably and non-obviously distinct invention, and maintains that this application may include more than one patentably and non-obviously distinct invention. The Applicant hereby asserts that the disclosure of this application may include more than one invention, and, in the event that there is more than one invention, that these inventions may be patentable and non-obvious one with respect to the other.

BRIEF DESCRIPTION OF THE DRAWINGS

The present application is described below by way of the figures of exemplified embodiments, in which, in detail.

DESCRIPTION OF EMBODIMENT OR EMBODIMENTS

Figure 5:
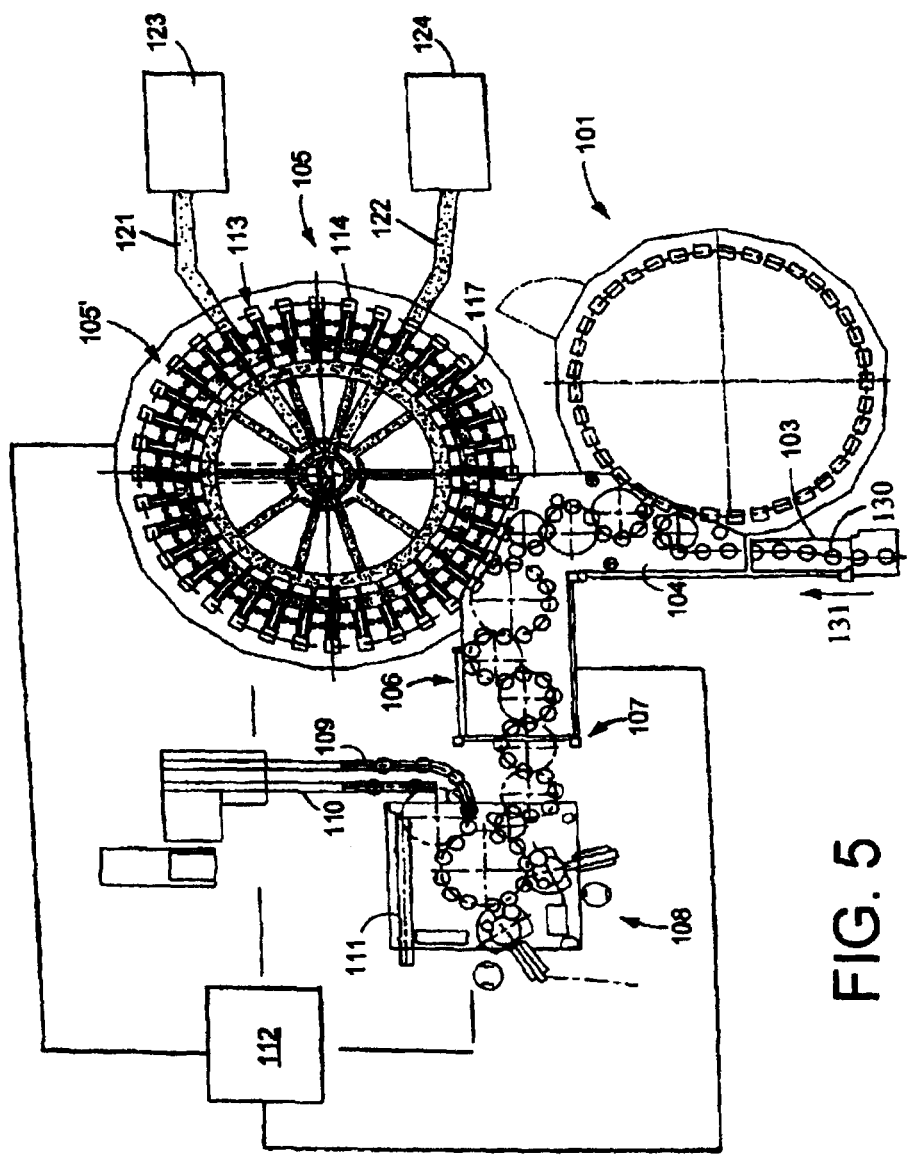
FIG. 5 shows schematically the main components of one possible embodiment example of a system for filling containers.

FIG. 5 shows schematically the main components of one possible embodiment example of a system for filling containers, specifically, a beverage bottling plant for filling bottles 130 with at least one liquid beverage, in accordance with at least one possible embodiment, in which system or plant could possibly be utilized at least one aspect, or several aspects, of the embodiments disclosed herein.

FIG. 5 shows a rinsing arrangement or rinsing station 101, to which the containers, namely bottles 130, are fed in the direction of travel as indicated by the arrow 131, by a first conveyer arrangement 103, which can be a linear conveyor or a combination of a linear conveyor and a starwheel. Downstream of the rinsing arrangement or rinsing station 101, in the direction of travel as indicated by the arrow 131, the rinsed bottles 130 are transported to a beverage filling machine 105 by a second conveyer arrangement 104 that is formed, for example, by one or more starwheels that introduce bottles 130 into the beverage filling machine 105.

The beverage filling machine 105 shown is of a revolving or rotary design, with a rotor 105', which revolves around a central, vertical machine axis. The rotor 105' is designed to receive and hold the bottles 130 for filling at a plurality of filling positions 113 located about the periphery of the rotor 105'. At each of the filling positions 103 is located a filling arrangement 114 having at least one filling device, element, apparatus, or valve. The filling arrangements 114 are designed to introduce a predetermined volume or amount of liquid beverage into the interior of the bottles 130 to a predetermined or desired level.

The filling arrangements 114 receive the liquid beverage material from a toroidal or annular vessel 117, in which a supply of liquid beverage material is stored under pressure by a gas. The toroidal vessel 117 is a component, for example, of the revolving rotor 105'. The toroidal vessel 117 can be connected by means of a rotary coupling or a coupling that permits rotation. The toroidal vessel 117 is also connected to at least one external reservoir or supply of liquid beverage material by a conduit or supply line. In the embodiment shown in FIG. 5, there are two external supply reservoirs 123 and 124, each of which is configured to store either the same liquid beverage product or different products. These reservoirs 123, 124 are connected to the toroidal or annular vessel 117 by corresponding supply lines, conduits, or arrangements 121 and 122. The external supply reservoirs 123, 124 could be in the form of simple storage tanks, or in the form of liquid beverage product mixers, in at least one possible embodiment.

As well as the more typical filling machines having one toroidal vessel, it is possible that in at least one possible embodiment there could be a second toroidal or annular vessel which contains a second product. In this case, each filling arrangement 114 could be connected by separate connections to each of the two toroidal vessels and have two individually-controllable fluid or control valves, so that in each bottle 130, the first product or the second product can be filled by means of an appropriate control of the filling product or fluid valves.

Downstream of the beverage filling machine 105, in the direction of travel of the bottles 130, there can be a beverage bottle closing arrangement or closing station 106 which closes or caps the bottles 130. The beverage bottle closing arrangement or closing station 106 can be connected by a third conveyer arrangement 107 to a beverage bottle labeling arrangement or labeling station 108. The third conveyor arrangement may be formed, for example, by a plurality of starwheels, or may also include a linear conveyor device.

In the illustrated embodiment, the beverage bottle labeling arrangement or labeling station 108 has at least one labeling unit, device, or module, for applying labels to bottles 130. In the embodiment shown, the labeling arrangement 108 is connected by a starwheel conveyer structure to three output conveyer arrangements: a first output conveyer arrangement 109, a second output conveyer arrangement 110, and a third output conveyer arrangement 111, all of which convey filled, closed, and labeled bottles 130 to different locations.

The first output conveyer arrangement 109, in the embodiment shown, is designed to convey bottles 130 that are filled with a first type of liquid beverage supplied by, for example, the supply reservoir 123. The second output conveyer arrangement 110, in the embodiment shown, is designed to convey bottles 130 that are filled with a second type of liquid beverage supplied by, for example, the supply reservoir 124. The third output conveyer arrangement 111, in the embodiment shown, is designed to convey incorrectly labeled bottles 130. To further explain, the labeling arrangement 108 can comprise at least one beverage bottle inspection or monitoring device that inspects or monitors the location of labels on the bottles 130 to determine if the labels have been correctly placed or aligned on the bottles 130. The third output conveyer arrangement 111 removes any bottles 130 which have been incorrectly labeled as determined by the inspecting device.

The beverage bottling plant can be controlled by a central control arrangement 112, which could be, for example, computerized control system that monitors and controls the operation of the various stations and mechanisms of the beverage bottling plant.

In the figures the reference 1 is given to a device for treating or sterilizing bottles with hydrogen peroxide. The device essentially comprises a rotor 3 that is rotatably driven about a vertical axis, to which rotor the bottles 2 to be treated are supplied via a container inlet 4 and from which rotor the treated or sterilized bottles 2 are removed via a container outlet 5 and are supplied to another use, for example to a filler to be filled with a liquid product.

A plurality of treatment heads 6 are provided on the periphery of the rotor 3 at regular angular spacings offset about the vertical machine or rotor axis. A bottle or container carrier 7 is assigned to each treatment head on the rotor, the respective bottle 2 being retained under the treatment head 6 on said bottle or container carrier during the treatment, in the specific embodiment represented the bottles 2, in the form of PET bottles, are suspended at a mouth flange at the side of the bottle.

The treatment, i.e. the sterilization of the bottles 2 is effected by using the hydrogen peroxide sterilization medium, which is generated in a known manner per se inside a mixing chamber that is formed in the treatment head 6 by injecting hydrogen peroxide, for example thirty-five percent hydrogen peroxide via at least one mixing nozzle into sterile air for forming a hydrogen peroxide/air aerosol and by subsequently heating said aerosol in an evaporator 6.2 to a temperature of, for example, one hundred forty-five degrees. A connection 6.1.1 for the sterile air and another connection 6.1.2 for the hydrogen peroxide are provided at the mixing chamber.

For the treatment, a tube 8 of the treatment head 6 that is positioned in an equi-axial manner to the axis of the respective bottle 1, is introduced into the bottle 2 and, by means of said tube, in an application phase, the hot hydrogen peroxide sterilization medium is first introduced into the interior of the bottle 2 in such a manner that an hydrogen peroxide condensation film forms on the inside surface of the bottle 2 through condensation. Following said application phase is the activating phase, where the hydrogen peroxide condensation film is activated by means of an application of energy, for example through the introduction of a hot, sterile gaseous and/or vaporous medium, for example through the introduction of hot sterile air via the tube 8, so that by means of decomposition reaction or splitting of hydrogen peroxide, free oxygen radicals are created, which react with any germs and/or contaminants that may be present in the respective bottle 2 and thus effect their sterilization.

In order, on the one hand, to optimize the consumption of hydrogen peroxide, on the other hand, however to achieve high quality sterilization, i.e. obtaining a high rate of sterilization in a reproducible manner, a precise or substantially precise and in one possible embodiment reproducible metering of the quantity of hydrogen peroxide that is supplied to the respective mixing chamber 6.1 via the connection 6.1.2 is indispensable.

Figure 1:
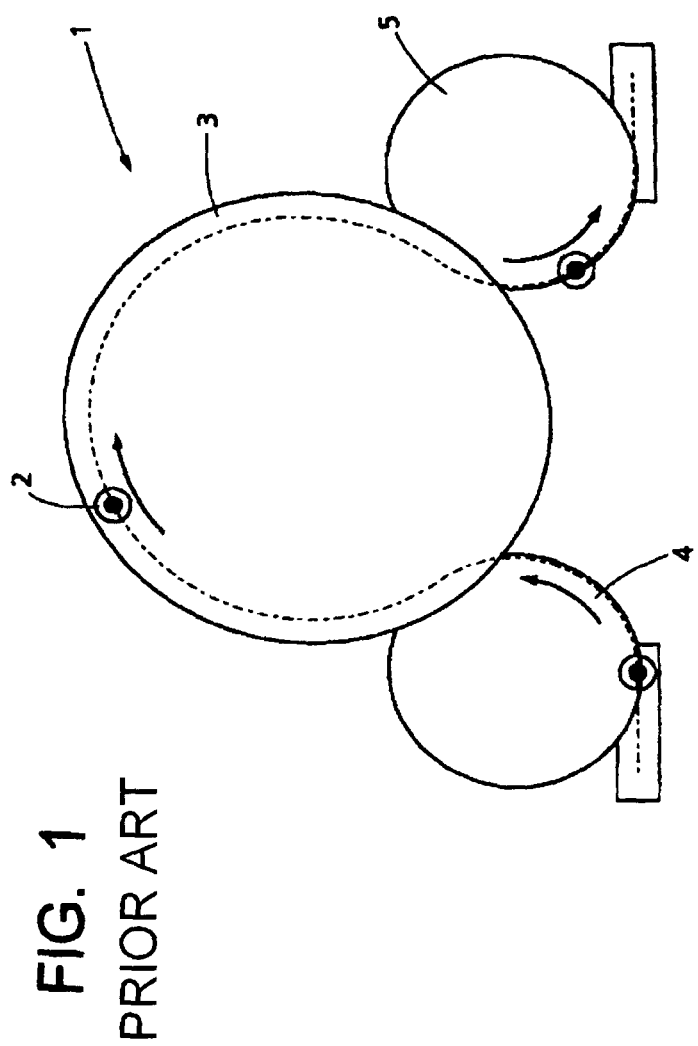
FIG. 1 is a very simplified representation and top view of a machine or device for treatment of packaging materials in the form of bottles.
Figure 2:
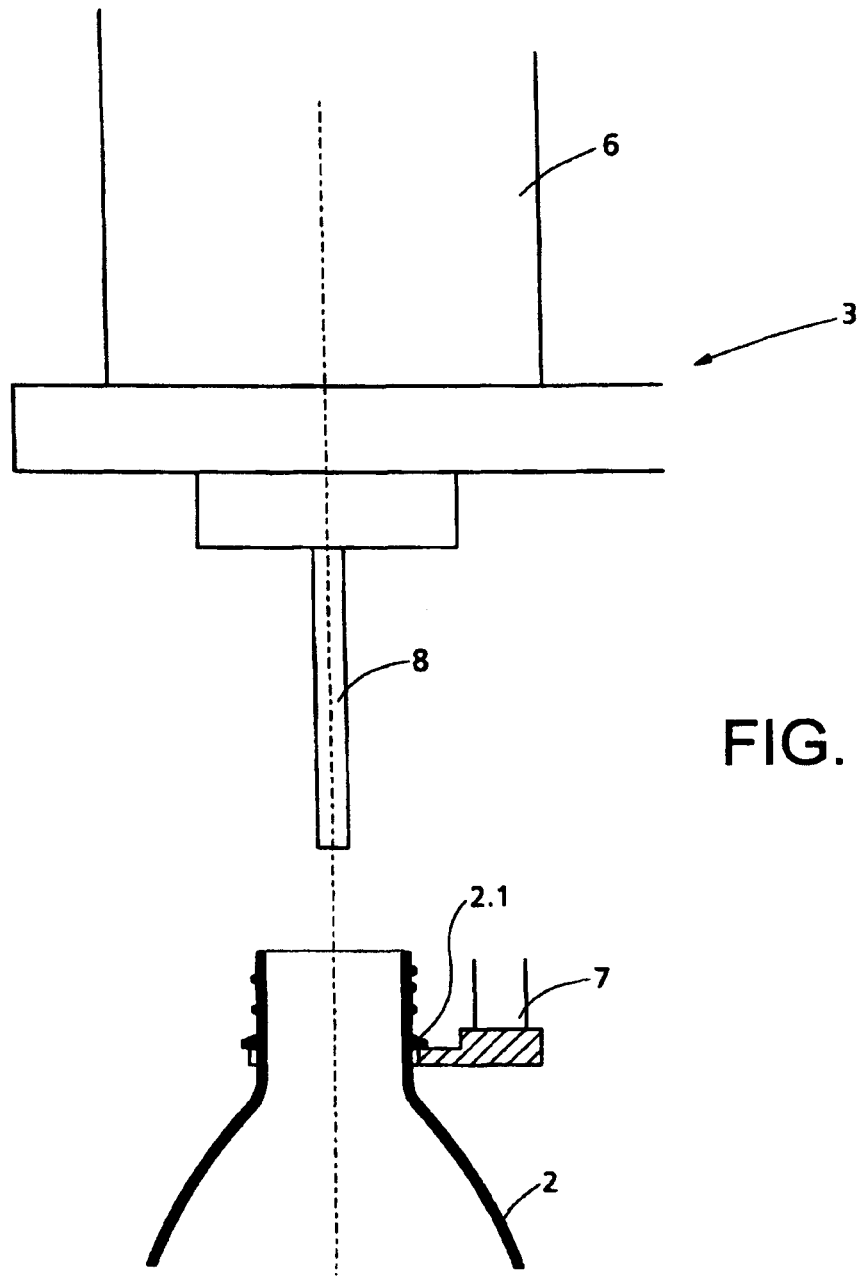
FIG. 2 is a simplified representation of a treatment head of the device in FIG. 1.
Figure 3:
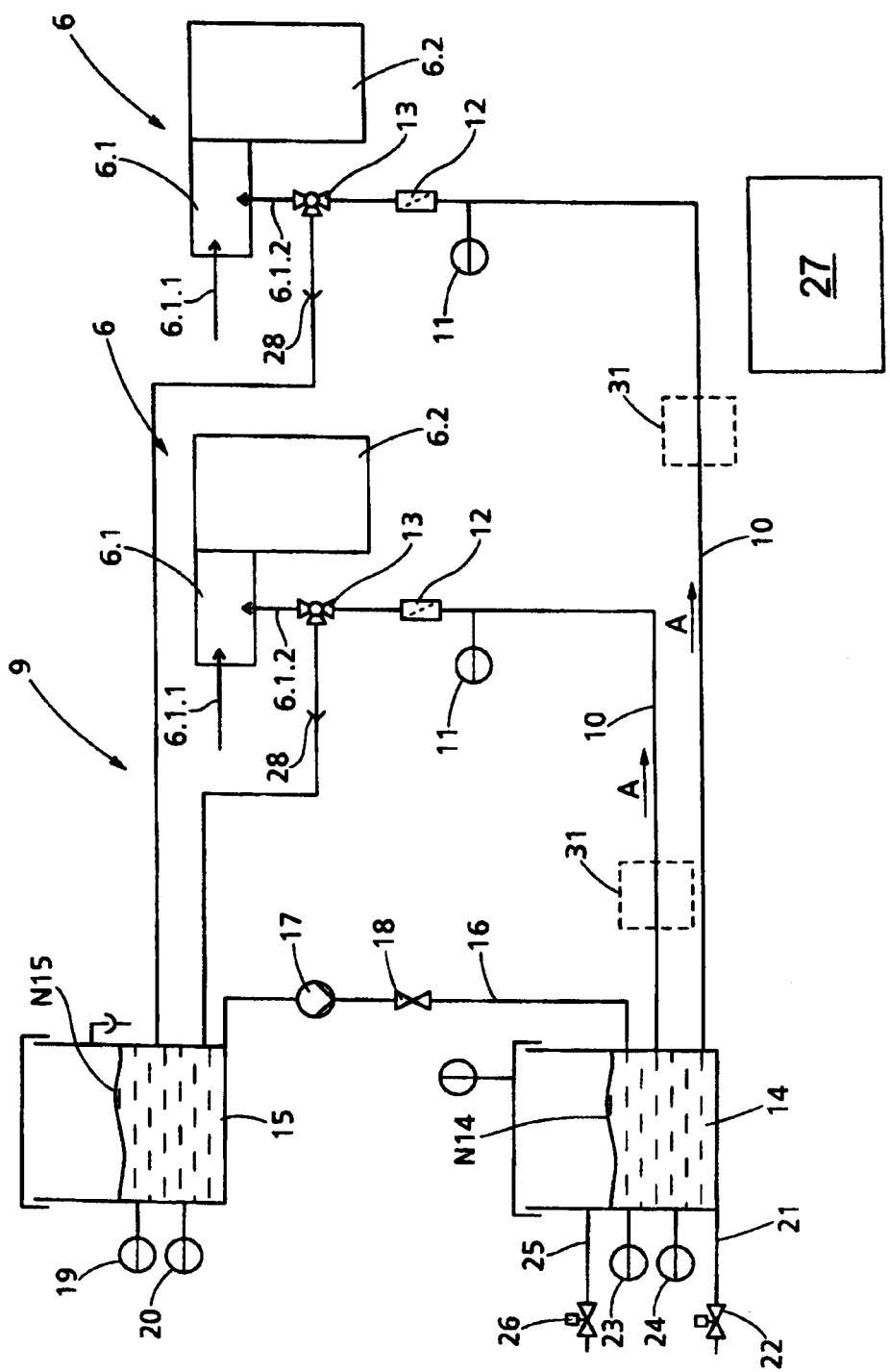
FIG. 3 is a functional representation of a system for the metered supplying of a treatment medium to a plurality of treatment heads of the device in FIG. 1.

FIG. 3 shows a simplified representation and block diagram of a supplying and metering system for supplying or respectively for the metered supplying of hydrogen peroxide to the individual treatment heads 6 of the device in FIG. 1, two of such treatment heads being shown in FIG. 3 for the purposes of simplifying the representation.

A fundamental problem in the metered supplying of hydrogen peroxide to the treatment heads is that hydrogen peroxide, as an unstable product, constantly or substantially constantly decomposes in water and oxygen even under normal ambient temperatures, the decomposition rate being increased even more in an uncontrollable manner in one possible embodiment through possible sudden pressure changes and/or pressure surges in a hydrogen peroxide-conducting system.

According to a finding underlying the present application, it is not possible to supply hydrogen peroxide from a storage container in a metered manner by means of metering pumps without further ado because, through the decomposition of the hydrogen peroxide in these types of pumps, but also in supply lines to or from the pumps, oxygen bubbles form, making precise or substantially precise metering very difficult or virtually impossible.

This problem may be solved through the embodiment of the metering and supplying system, identified in general by the reference 9 in FIG. 3. This system provides a hydrogen peroxide cycle for each treatment head 6, said hydrogen peroxide cycle being formed in each case by the ring line 10, which is traversed constantly or substantially constantly by the hydrogen peroxide in the direction of the arrow A during the operation of the device 1 and in which are provided, in the direction of flow A one after the other, a flow meter 11, a filter 12 and a metering valve 13 in the form of a ⅔ way valve. The latter is positioned with an entry and one of two exits in the ring line 10 and is connected by its second exit to the connection 6.1.2 of the respective treatment head. Each ring line 10 extends between a storage or supplying container 14, which houses the hydrogen peroxide under pressure (metering pressure) and from which the hydrogen peroxide flows into the ring line 10, as well as a collecting container 15 for collecting the hydrogen peroxide that flows back via the ring lines 10 and for separating off oxygen at the interface or hydrogen peroxide level between the liquid hydrogen peroxide in the liquid space of the collecting container 15 and the gas space of the collecting container 15 formed above the hydrogen peroxide level. The separated oxygen is then, for example, conducted into the atmosphere or supplied for a further use, for example to a device for generating ozone for sterilization purposes. From the collecting container 15, the hydrogen peroxide is returned to the storage or supplying container 14 via a connecting line 16. A pump 17 is provided in series with a non-return valve 18 in the connecting line 16 for this purpose.

The pressure in the collecting container 15 is lower than the metering pressure in the supplying container 14 and corresponds, for example, to atmospheric pressure. The pump 17 is controlled in dependence on the output signal of two level switches 19 and 20 so that the level $N_{15}$ of the liquid level of the hydrogen peroxide in the partly filled collecting container 15 is held between a predetermined maximum value and a predetermined minimum value. The supplying container 14 is connected via a supply line 21 with control valve 22 to a source that provides hydrogen peroxide under pressure. In addition, two level switches 23 and 24 are provided at the storage or supplying container 14, via which the supply of hydrogen peroxide to the equally partly filled supplying container 14 is regulated by corresponding actuation of the control valve 22, in such a manner that the level $N_{14}$ of the liquid level of the hydrogen peroxide in the supplying container 14 is always or substantially always between a maximum and a minimum value. The gas space formed above the liquid level in the supplying container 14 is connected via a supply line 25 with control valve 26 to a source, which provides sterile air under pressure. In dependence on the signal of a pressure meter provided at the supplying container 14, the control valve 26 is controlled in such a manner that a constant or substantially constant metering pressure is realized in the supplying container 14. In principle, it is also possible to realize the valve 26 as a reverse ventilating pressure reducing valve for regulating the pressure in the storage container 14.

The method of operation of the metering and supplying system 9 can be described as follows:

The metering valves 13 are, for example, realized such that, in the non-activated state, they enable a continuous flow of hydrogen peroxide through the individual ring lines 10 from the supplying container 14 into the collecting container 15. This cycle essentially ensures or promotes that in each ring line 10, in one possible embodiment also in the line section in the direction of flow upstream of the respective metering valve 13, there is exclusively or almost exclusively hydrogen peroxide without or substantially without oxygen or gas bubbles, and that oxygen split off from the hydrogen peroxide separates on the liquid level or on the interface in the collecting container 15.

For the metered dispensing of the hydrogen peroxide to the respective treatment head 6 or to the mixing chamber 6.1 at that location, the relevant metering valve 13 is in one possible embodiment periodically activated and then deactivated, for example in the activated state the volume flow of the hydrogen peroxide being detected by means of the flow meter 11 and the metering valve 13 being controlled in dependence on a corresponding measuring signal supplied to the control device 27, such that the necessary and/or desired metering of hydrogen peroxide at the respective treatment head 6 is achieved, the metering pressure prevailing in the ring line 10 also being taken into consideration for this metering or for this controlled opening and closing of the metering valves 13, as is also, among other things, the volume flow of the sterile air flowing to the respective mixing chamber 6.1.

In order to avoid, restrict, and/or minimize oxygen separating off or oxygen separating off in an increased manner from the hydrogen peroxide at least in the part of the respective ring line 10 upstream of the metering valve 13 when said valve is activated and deactivated, and in order to essentially ensure or promote that the metering pressure is pending at the metering valves 13, a throttle 28 is provided in each ring line 10 in the direction flow following the metering valve 13 or at the corresponding exit of the metering valve 13, said throttle being selected or adjusted such that the same or approximately the same flow resistance is produced for the hydrogen peroxide flow at the two exits of each metering valve 13, that is also the volume flow of the hydrogen peroxide in the section of the ring line 10 upstream of the respective metering valve is independent of the state of said valve and consequently no pressure surges or abrupt pressure changes are produced in the respective ring line 10 upstream of the metering valve 13.

A characteristic of the metering and supplying system 9 is also that the conveying of the hydrogen peroxide through the ring lines 10 and in one possible embodiment also through the metering valves 13 is effected exclusively by means of the metering or head pressure in the supplying container 14, no pumps being provided in the actual cycle of the hydrogen peroxide between the two containers 14 and 15. This method of operation achieves in one possible embodiment a uniform flow that is free of the pressure fluctuations caused normally by pumps.

The connection between the metering valve 13 and the connection 6.1.2 or the metering nozzle of the mixing chamber 6.12 of the associated treatment head 6 is kept as short as possible in order to keep the dwell time of the hydrogen peroxide within said connection and consequently the splitting of oxygen from the oxygen peroxide as small as possible.

Also, the inlets and outlets for each of the storage tank 14 and the collecting tank 15 should be disposed as far apart as possible in order to minimize the impact the inlet may have on the outlet. To further explain, the hydrogen peroxide flowing through the inlet or inlets into the collecting tank 15 has oxygen bubbles forming or entrained therein, which oxygen bubbles will escape from the hydrogen peroxide while the hydrogen peroxide is temporarily stored in the collecting tank 15. At the same time, hydrogen peroxide which is to be substantially free of oxygen bubbles is being pumped via an outlet and the return line into the storage tank 14. In the event that the inlet in the collecting tank 15 is near the outlet of the collecting tank 15, the incoming hydrogen peroxide, which contains an undesirable number of oxygen bubbles, might be drawn prematurely through the outlet before the oxygen bubbles have time to escape. However, if the inlet and outlet are positioned a sufficient distance apart, the chances of the incoming hydrogen peroxide being drawn out prematurely could be minimized, and thus would promote only the outlet of hydrogen peroxide that is substantially free of oxygen bubbles.

Figure 4:
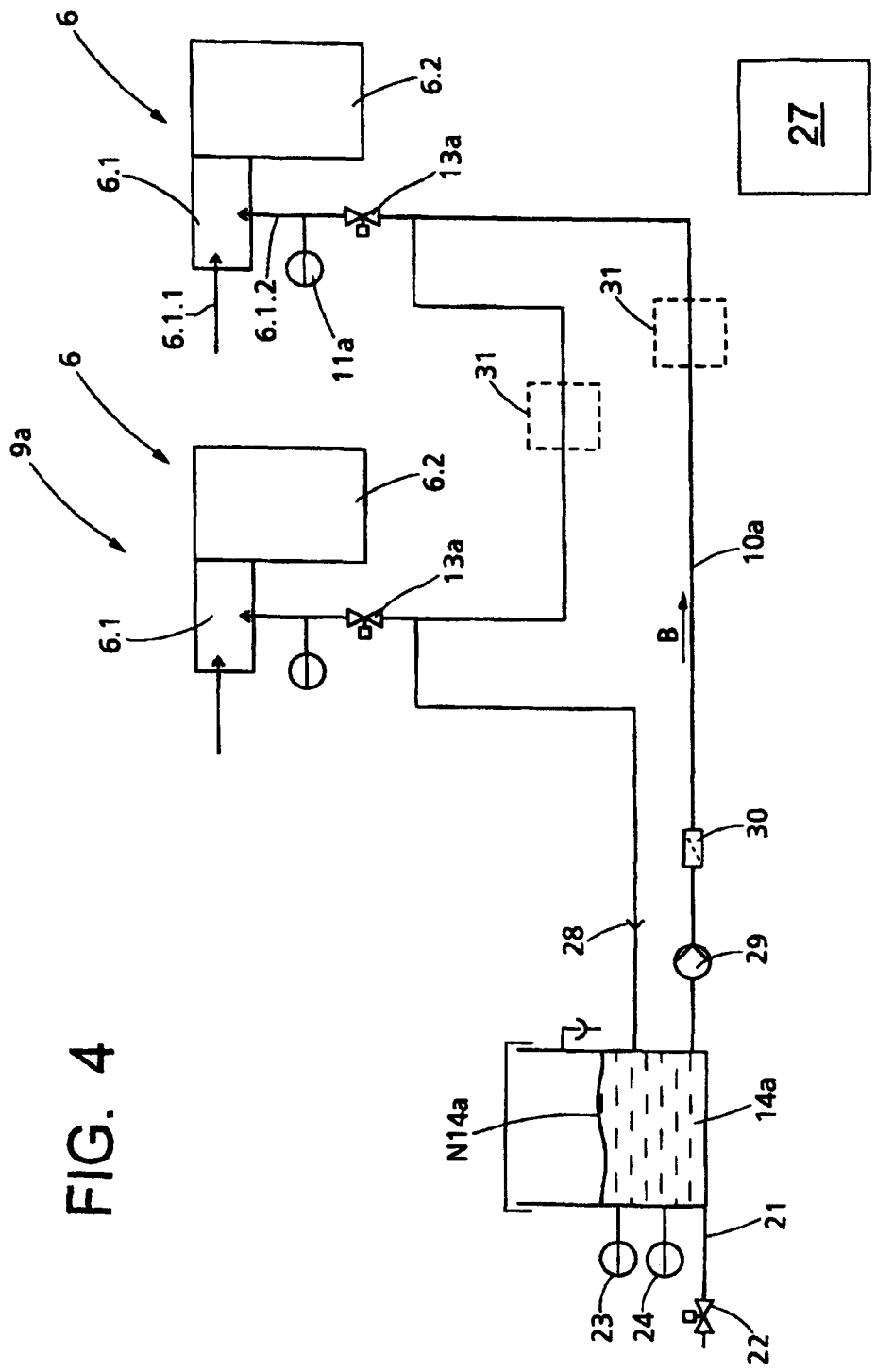
FIG. 4 is a representation as in FIG. 3 with another specific embodiment of the system according to the present application.

FIG. 4 shows, in the form of another specific embodiment, a metering system 9a, which is also suitable for use with the device 1, once again two treatment heads 6 also being represented in FIG. 4 for reasons of clarity.

An essential difference to the metering and supplying system 9 is that the metering and supplying system 9a just has one single ring line 10a for the treatment heads 6, and that said ring line 10a is connected to the supplying container 14a via a pump 29, for example a centrifugal pump, and via a filter 30 that is connected in series with the pump outlet, said supplying container housing the hydrogen peroxide in the pressureless state, i.e. at atmospheric pressure. The ring line 10a is returned to the storage container 14a via a throttle 28a so that, with the pump 29 switched on, a hydrogen peroxide cycle is produced out of the storage container 14a through the pump 29, the filter 20 and the throttle 28a back into the storage container 14a in the direction of the arrow B. In this hydrogen peroxide cycle or circuit, a metering valve 13a is provided in the direction of flow after the pump 29 or after the filter 30 and before the throttle 29a for each treatment head 6, said metering valve is opened and closed in a controlled manner by the control device 27, that is not changed-over between two exits contrary to the metering valves 13. In this specific embodiment, a flow meter 11a for each treatment head 6 is provided separately in the connecting line between the respective metering valve 13a and the mixing chamber 6.1 or the mixing nozzle at that location, which flow meter with the metering valve 13a activated, i.e. open, detects the quantity of hydrogen peroxide flowing to the respective treatment head 6 and supplies a corresponding measuring signal for controlling the metering or the associated metering valve 13a to the control device 27. In the case of the specific embodiment also, the respective connection between the metering valve 13a and the mixing chamber 6.1 of the associated treatment head 6 is as short as possible in order to keep the dwell time of the hydrogen peroxide in this connection and consequently the splitting of oxygen as small as possible.

The supplying container 14a, in its turn, is connected via the supply line 21 with the control valve 22 to a supplying source for the hydrogen peroxide. The two level switches 23 and 24 are provided once again for regulating the level $N_{14A}$ of the liquid level in the supplying container 14a or for controlling the control valve 22.

The method of operation of the metering and supplying system 9a can be described as follows:

With the pump 29 switched on, a continuous hydrogen peroxide cycle through the ring line 10a from the storage container 14a and then back again into said storage container is achieved and at the same time, in one possible embodiment, achieving that oxygen separating off from the hydrogen peroxide is separated in the supplying container 14a at the liquid level at that location or at the interface at that location and, for example, is conducted into the atmosphere or is supplied to another use, for example to a device for generating ozone for sterilizations purposes. The hydrogen peroxide circulating in the ring line 10a is consequently free or at least substantially free of gas and oxygen bubbles. The hydrogen peroxide is metered in a controlled manner by opening and closing the metering valves 13a, with this metering or with this controlled opening and closing of the metering valves 13a by the control device 27 obviously once again the metering pressure prevailing in the ring line 10a and generated by the pump 29 is also taken into consideration, as is also, among other things, the volume flow of the sterile air flowing to the respective mixing chamber 6.1.

The cross-section of the ring line 10a is selected sufficiently large so that pressure losses and/or pressure fluctuations and/or changes in the volume flow of the hydrogen peroxide caused by the periodic, but controlled opening and closing of the metering valves 13a are insignificant and, in one possible embodiment, so that the identical or substantially identical, constant or substantially constant or regulated metering pressure is also pending in each case at each metering valve 13*a*. This means that the metering volume is then exclusively dependent on the switching or opening time of the respective metering valve 13*a* and a separating off of oxygen from the hydrogen peroxide, caused by pressure loss and/or pressure fluctuations and/or changes in the volume flow, is prevented, restricted, and/or minimized. The throttle 28*a*, in its turn, is adjusted such that the flow resistance generated by said throttle is identical or substantially identical to that flow resistance that the mixing chambers 6.1, actuated via the metering valves 13*a*, in total or in series, form for the flow of hydrogen peroxide.

The present application has been described above by way of possible embodiments. It is obvious that changes and conversions are possible without departing from the teaching concept underlying the present application.

The present application has been explained above in conjunction with hydrogen peroxide sterilization of bottles 2. The present application, in one possible embodiment also the described metering systems 9 and 9*a*, however, are equally suitable for hydrogen peroxide sterilization of other packaging or packaging materials, such as, for example screw closures.

In addition, it has been assumed above that when using the supplying container 14 that is impinged upon with metering pressure, a specific ring line 10 with a metering valve 13 in the form of a ⅔ way valve is provided for each treatment head 6. However, in principle it is also possible, when using a supplying container 14 that is impinged upon with pressure, to provide a common ring line corresponding to the ring line 10*a* for the treatment heads 6 or for a group of treatment heads 6, with control valves that are simply controllable between a closed state and an open state at least during the dosing procedure.

In addition, in principle it is also possible, with a pressureless supplying container 14*a*, to provide in each case an independent ring line with metering valve for each treatment head 6 or for a group of treatment heads 6, the metering pressure then being generated by a pump that is positioned in each ring line or by a pump that is common to all or to a plurality of ring lines.

In addition, it can be possible to provide in the respective ring line 10 that is associated independently with each treatment head or in a ring line 10*a* that is common to the treatment heads or to a group of treatment heads, at least one additional gas separator for removing oxygen that has split off from the hydrogen peroxide, in one possible embodiment in each case in the direction of flow of the hydrogen peroxide upstream of the relevant metering valve, as is indicated in FIGS. 3 and 4 by the broken lines at 31.

In addition it can be possible to monitor and regulate, in a targeted manner, the quantity of hydrogen peroxide supplied to each individual treatment head 6. To this end, it is provided to evaluate the data supplied by each individual flow meter 11*a* within a control unit and to use it for actuating the associated metering valve 13*a*.

Figure 6:
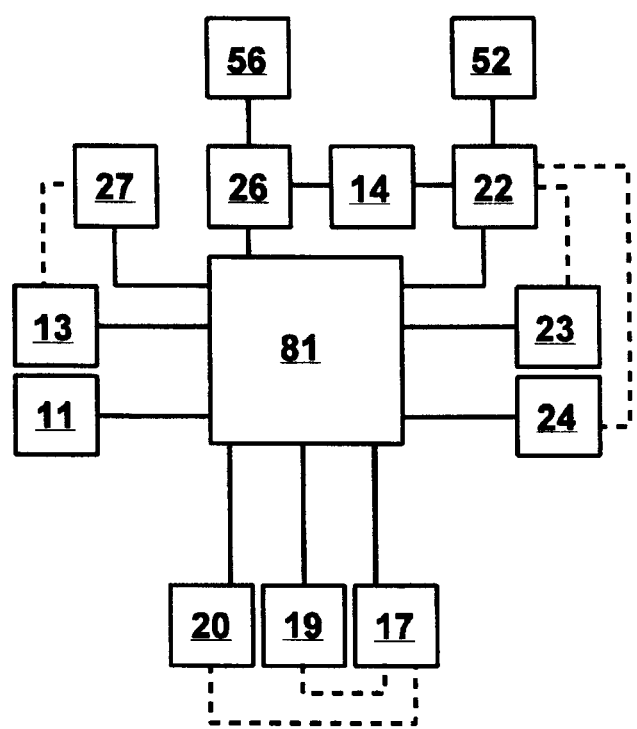
FIG. 6 shows a block diagram representing the different components of at least one possible embodiment.

FIG. 6 shows a block diagram representing the different components of at least one possible embodiment. A central control 81, such as a computer control, monitors and controls the operation of several different portions of the overall system. The central control 81 is connected to the flow meters 11, metering valves 13, pump 17, level switches 19, 20, 23, 24, control valves 22, 26, and control device 27, so as to both control and/or receive and coordinate information obtained by the different components. Also shown are a hydrogen peroxide supply or source 52, which is connected via the control valve 22 to supply hydrogen peroxide to the storage or supply container 14, and a pressurized gas supply or source 56, which is connected via the control valve 26 to supply pressurized gas, such as sterile air, to the storage or supply container 14. In addition, FIG. 6 shows the operational connections between different components in dashed lines. Specifically, the operation of the control valve 22 is dependent on information received from the level switches 23, 24, and the operation of the pump 17 is dependent on information received from the level switches 19, 20. Finally, the operation of the metering valves 13 is dependent on a signal of the control device 27.

In one possible embodiment, in addition to a central storage tank, there is also a central collecting container that is different from the storage container, whereby a mechanical transport means no longer has to be provided in the ring line. Therefore, in the feed line, the disadvantageous input of energy via the drive means of a pump can be eliminated, and both in the head space of the collecting container (15) as well as in the head space of the storage container (14), a degasification can take place which has no influence on the dosing points.

In at least one possible embodiment of a method according to the present application, although the sterilizing agent is transported from the collecting container 15 by means of a pump into the storage container 14 which is under a higher pressure, the necessary calming of the fluid or the degasification which is some cases inevitable can take place in the storage container 14. At least one embodiment of the system described herein is structurally simple and therefore economical and offers two calming chambers in the form of two large fluid spaces or tanks or containers in which a degasification can take place and the entrainment of gas bubbles upstream to the dosing points is essentially prevented or minimized.

The present application relates to a dosing and supply system for the dosed supply of hydrogen peroxide to treatment heads of a device for hydrogen peroxide sterilization of packaging materials, having at least one supply container providing the hydrogen peroxide and having a controllable connection between the at least one supply container and the respective treatment head; according to the present application, the controllable connection is formed by at least one loop that, along with the at least one supply container, forms a circuit or cycle for the hydrogen peroxide, and the respective treatment head is connected via at least one dosing valve to the at least one loop.

One feature or aspect of an embodiment is believed at the time of the filing of this patent application to possibly reside broadly in a metering and supplying system for the metered supplying of hydrogen peroxide to treatment heads 6 of a device for hydrogen peroxide sterilization of packaging materials 2, said metering and supplying system including at least one storage container 14, 14*a* providing the hydrogen peroxide and a controllable connection between the at least one storage container 14, 14*a* and the respective treatment head 6, wherein the controllable connection is formed by at least one ring line 10, 10*a*, which, together with the at least one storage container 14, 14*a*, forms a cycle or circuit for the hydrogen peroxide, and in that the respective treatment head 6 is connected via at least one metering valve 13, 13*a* to the at least one ring line 10, 10*a*.

Another feature or aspect of an embodiment is believed at the time of the filing of this patent application to possibly reside broadly in the metering and supplying system, wherein via the respective metering valve 13, 13*a* a mixing chamber 6.1 or at least one mixing nozzle of the respective treatment head 6 positioned in said mixing chamber is connected to the at least one ring line 10, 10*a*, by means of which mixing nozzle a mixing of the hydrogen peroxide is effected with a gaseous and/or vaporous carrier, for example with air, which is also supplied to the mixing chamber 6.1.

Yet another feature or aspect of an embodiment is believed at the time of the filing of this patent application to possibly reside broadly in the metering and supplying system, wherein in the cycle formed by the at least one ring line 10, in addition to the at least one storage container 14, at least one collecting container is provided for collecting the hydrogen peroxide returned via the at least one ring line 10.

Still another feature or aspect of an embodiment is believed at the time of the filing of this patent application to possibly reside broadly in the metering and supplying system, wherein the at least one collecting container 15 communicates with the storage container 14 via a connecting line 16.

A further feature or aspect of an embodiment is believed at the time of the filing of this patent application to possibly reside broadly in the metering and supplying system, wherein to generate a necessary and/or desired metering pressure, the supplying container 14 can be impinged upon with a regulated pressure.

Another feature or aspect of an embodiment is believed at the time of the filing of this patent application to possibly reside broadly in the metering and supplying system, wherein the pressure in the collecting container 15 is less than the metering pressure pending at the respective metering valve 13, 13a, and in that a pump 17 is provided in the connecting line between the collecting container 15 and the supplying container.

Yet another feature or aspect of an embodiment is believed at the time of the filing of this patent application to possibly reside broadly in the metering and supplying system, wherein at least one pump 29 is provided to generate the metering pressure pending at the metering valve 13.

Still another feature or aspect of an embodiment is believed at the time of the filing of this patent application to possibly reside broadly in the metering and supplying system, wherein the at least one pump 29 generating the metering pressure is a component of the at least one ring line 10a.

A further feature or aspect of an embodiment is believed at the time of the filing of this patent application to possibly reside broadly in the metering and supplying system, wherein the at least one ring line 10a is connected at both ends to the at least one supplying container 14a.

Another feature or aspect of an embodiment is believed at the time of the filing of this patent application to possibly reside broadly in the metering and supplying system, wherein means for discharging gaseous decomposition products of the hydrogen peroxide are provided in the hydrogen peroxide cycle.

Yet another feature or aspect of an embodiment is believed at the time of the filing of this patent application to possibly reside broadly in the metering and supplying system, wherein the means for separating or discharging the gaseous decomposition products of the hydrogen peroxide are formed by gas separators that are provided in the hydrogen peroxide cycle, for example gas separators 31 positioned in the at least one ring line 10, 10a.

Still another feature or aspect of an embodiment is believed at the time of the filing of this patent application to possibly reside broadly in the metering and supplying system, wherein the means for discharging the gaseous decomposition products of the hydrogen peroxide are formed by the interface between a liquid space and a gas space in a housing or container, for example in the at least one supplying container 14, 14a and/or in the at least one collecting container 15.

A further feature or aspect of an embodiment is believed at the time of the filing of this patent application to possibly reside broadly in the metering and supplying system, wherein one ring line 10 is provided in each case for each treatment head 6 or for a group of treatment heads 6.

One feature or aspect of an embodiment is believed at the time of the filing of this patent application to possibly reside broadly in the metering and supplying system, wherein the at least one storage container 14 and/or the at least one collecting container 15 is provided in common for the ring lines 10.

Another feature or aspect of an embodiment is believed at the time of the filing of this patent application to possibly reside broadly in the metering and supplying system, wherein a common ring line 10a is provided for the treatment heads.

Yet another feature or aspect of an embodiment is believed at the time of the filing of this patent application to possibly reside broadly in the metering and supplying system, wherein the metering valves 13 are at least in part change-over valves, which are controllable at least during the metering procedure between a state enabling the volume flow through the ring line 10a and a state conducting the volume flow to the relevant treatment head 6.

Still another feature or aspect of an embodiment is believed at the time of the filing of this patent application to possibly reside broadly in the metering and supplying system, wherein the metering valves 13a are at least in part valves that are controllable at least during the metering procedure between an open state and a closed state.

A further feature or aspect of an embodiment is believed at the time of the filing of this patent application to possibly reside broadly in the metering and supplying system, wherein in the two states of the respective metering valve 13 the flow resistance for the hydrogen peroxide flowing through said valve is identical or substantially identical.

Another feature or aspect of an embodiment is believed at the time of the filing of this patent application to possibly reside broadly in a device for hydrogen peroxide sterilization of packaging materials 2, said device having a plurality of treatment heads 6 for the introduction in each case of a heated hydrogen peroxide sterilization medium, comprising hydrogen peroxide and a vaporous and/or gaseous carrier, into the packaging materials 2 to be sterilized and for the subsequent activating of the hydrogen peroxide sterilization medium, and having a metering and supplying system 9, 9a for the metered supplying of the hydrogen peroxide to the treatment heads 6, wherein the metering and supplying system 9, 9a is realized according to the present application.

One feature or aspect of an embodiment is believed at the time of the filing of this patent application to possibly reside broadly in a metering and supplying system for the metered supplying of hydrogen peroxide to treatment heads 6 of a device for hydrogen peroxide sterilization of packaging materials 2, said metering and supplying system including at least one storage container 14, 14a providing the hydrogen peroxide and a controllable connection between the at least one storage container 14, 14a and the respective treatment head 6, whereby the controllable connection is formed by at least one ring line 10, 10a, which, together with the at least one storage container 14, 14a, forms a cycle or circuit for the hydrogen peroxide, and in that the respective treatment head 6 is connected via at least one metering valve 13, 13a to the at least one ring line 10, 10a, wherein the cycle formed by the at least one ring line 10, in addition to the at least one storage container 14, at least one central collecting container 15 is provided for collecting the hydrogen peroxide returned via the at least one ring line 10.

Another feature or aspect of an embodiment is believed at the time of the filing of this patent application to possibly reside broadly in a method for hydrogen peroxide sterilization of packaging materials 2, said device having a plurality of treatment heads 6 for the introduction in each case of a heated hydrogen peroxide sterilization medium, comprising hydrogen peroxide and a vaporous and/or gaseous carrier, into the packaging materials 2 to be sterilized and for the subsequent activating of the hydrogen peroxide sterilization medium, and having a metering and supplying system 9, 9*a* for the metered supplying of the hydrogen peroxide to the treatment heads 6, wherein the metering and supplying system 9, 9*a* is used according to the present application.

Yet another feature or aspect of an embodiment is believed at the time of the filing of this patent application to possibly reside broadly in a metering and supplying system for the metered supplying of hydrogen peroxide to treatment heads 6 of a device for hydrogen peroxide sterilization of packaging materials 2, said metering and supplying system including at least one storage container 14, 14*a* providing the hydrogen peroxide and a controllable connection between the at least one storage container 14, 14*a* and the respective treatment head 6, whereby the controllable connection is formed by at least one ring line 10, 10*a*, which, together with the at least one storage container 14, 14*a*, forms a cycle or circuit for the hydrogen peroxide, and in that the respective treatment head 6 is connected via at least one metering valve 13, 13*a* to the at least one ring line 10, 10*a* wherein in the cycle formed by the at least one ring line 10, in addition to the at least one storage container 14, at least one central collecting container 15 is provided for collecting the hydrogen peroxide returned via the at least one ring line 10, and to generate a necessary and/or desired metering pressure, the supplying container 14 can be impinged upon with a regulated pressure.

Still another feature or aspect of an embodiment is believed at the time of the filing of this patent application to possibly reside broadly in a metering and supplying system for the metered supplying of hydrogen peroxide to treatment heads 6 of a device for hydrogen peroxide sterilization of packaging materials 2, said metering and supplying system including at least one storage container 14, 14*a* providing the hydrogen peroxide and a controllable connection between the at least one storage container 14, 14*a* and the respective treatment head 6, whereby the controllable connection is formed by at least one ring line 10, 10*a*, which, together with the at least one storage container 14, 14*a*, forms a cycle or circuit for the hydrogen peroxide, and in that the respective treatment head 6 is connected via at least one metering valve 13, 13*a* to the at least one ring line 10, 10*a*, wherein in the cycle formed by the at least one ring line 10, in addition to the at least one storage container 14, at least one central collecting container 15 is provided for collecting the hydrogen peroxide returned via the at least one ring line 10, and to generate a necessary and/or desired metering pressure, the supplying container 14 can be impinged upon with a regulated pressure.

A further feature or aspect of an embodiment is believed at the time of the filing of this patent application to possibly reside broadly in the metering and supplying system, wherein via the respective metering valve 13, 13*a* a mixing chamber 6.1 or at least one mixing nozzle of the respective treatment head 6 positioned in said mixing chamber is connected to the at least one ring line 10, 10*a*, by means of which mixing nozzle a mixing of the hydrogen peroxide is effected with a gaseous and/or vaporous carrier, for example with air, which is also supplied to the mixing chamber 6.1.

Another feature or aspect of an embodiment is believed at the time of the filing of this patent application to possibly reside broadly in the metering and supplying system, wherein the at least one collecting container 15 communicates with the storage container 14 via a connecting line 16.

Yet another feature or aspect of an embodiment is believed at the time of the filing of this patent application to possibly reside broadly in the metering and supplying system, wherein the pressure in the collecting container 15 is less than the metering pressure pending at the respective metering valve 13, 13*a*, and in that a pump 17 is provided in the connecting line between the collecting container 15 and the supplying container.

Still another feature or aspect of an embodiment is believed at the time of the filing of this patent application to possibly reside broadly in the metering and supplying system, wherein at least one pump 29 is provided to generate the metering pressure pending at the metering valve 13.

A further feature or aspect of an embodiment is believed at the time of the filing of this patent application to possibly reside broadly in the metering and supplying system, wherein the at least one pump 29 generating the metering pressure is a component of the at least one ring line 10*a*.

Another feature or aspect of an embodiment is believed at the time of the filing of this patent application to possibly reside broadly in the metering and supplying system, wherein means for discharging gaseous decomposition products of the hydrogen peroxide are provided in the hydrogen peroxide cycle.

Yet another feature or aspect of an embodiment is believed at the time of the filing of this patent application to possibly reside broadly in the metering and supplying system, wherein the means for separating or discharging the gaseous decomposition products of the hydrogen peroxide are formed by gas separators that are provided in the hydrogen peroxide cycle, for example gas separators 31 positioned in the at least one ring line 10, 10*a*.

Still another feature or aspect of an embodiment is believed at the time of the filing of this patent application to possibly reside broadly in the metering and supplying system, wherein the means for discharging the gaseous decomposition products of the hydrogen peroxide are formed by the interface between a liquid space and a gas space in a housing or container, for example in the at least one supplying container 14, 14*a* and/or in the at least one collecting container 15.

A further feature or aspect of an embodiment is believed at the time of the filing of this patent application to possibly reside broadly in the metering and supplying system, wherein one ring line 10 is provided in each case for each treatment head 6 or for a group of treatment heads 6.

One feature or aspect of an embodiment is believed at the time of the filing of this patent application to possibly reside broadly in the metering and supplying system, wherein the at least one storage container 14 and/or the at least one collecting container 15 is provided in common for the ring lines 10.

Another feature or aspect of an embodiment is believed at the time of the filing of this patent application to possibly reside broadly in the metering and supplying system, wherein a common ring line 10*a* is provided for the treatment heads.

Yet another feature or aspect of an embodiment is believed at the time of the filing of this patent application to possibly reside broadly in the metering and supplying system, wherein the metering valves 13 are at least in part change-over valves, which are controllable at least during the metering procedure between a state enabling the volume flow through the ring line 10*a* and a state conducting the volume flow to the relevant treatment head 6.

Still another feature or aspect of an embodiment is believed at the time of the filing of this patent application to possibly reside broadly in the metering and supplying system, wherein the metering valves 13a are at least in part valves that are controllable at least during the metering procedure between an open state and a closed state.

A further feature or aspect of an embodiment is believed at the time of the filing of this patent application to possibly reside broadly in the metering and supplying system wherein in the two states of the respective metering valve 13 the flow resistance for the hydrogen peroxide flowing through said valve is identical or substantially identical.

Another feature or aspect of an embodiment is believed at the time of the filing of this patent application to possibly reside broadly in the method for hydrogen peroxide sterilization of packaging materials 2, said device having a plurality of treatment heads 6 for the introduction in each case of a heated hydrogen peroxide sterilization medium, comprising hydrogen peroxide and a vaporous and/or gaseous carrier, into the packaging materials 2 to be sterilized and for the subsequent activating of the hydrogen peroxide sterilization medium, and having a metering and supplying system 9, 9a for the metered supplying of the hydrogen peroxide to the treatment heads 6, wherein the metering and supplying system 9, 9a is used according to the present application.

The components disclosed in the various publications, disclosed or incorporated by reference herein, may possibly be used in possible embodiments of the present invention, as well as equivalents thereof.

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

The appended drawings in their entirety, including all dimensions, proportions and/or shapes in at least one embodiment of the invention, are accurate and are hereby included by reference into this specification.

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

All, or substantially all, of the components and methods of the various embodiments may be used with at least one embodiment or all of the embodiments, if more than one embodiment is described herein.

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

All of the patents, patent applications and publications recited herein, and in the Declaration attached hereto, are hereby incorporated by reference as if set forth in their entirety herein.

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

It will be understood that the examples of patents, published patent applications, and other documents which are included in this application and which are referred to in paragraphs which state "Some examples of . . . which may possibly be used in at least one possible embodiment of the present application . . ." may possibly not be used or useable in any one or more embodiments of the application.

The sentence immediately above relates to patents, published patent applications and other documents either incorporated by reference or not incorporated by reference.

Some examples of bottling systems, which may be used or adapted for use in at least one possible embodiment of the present may be found in the following U.S. patents assigned to the Assignee herein, namely: U.S. Pat. Nos. 4,911,285; 4,944,830; 4,950,350; 4,976,803; 4,981,547; 5,004,518; 5,017,261; 5,062,917; 5,062,918; 5,075,123; 5,078,826; 5,087,317; 5,110,402; 5,129,984; 5,167,755; 5,174,851; 5,185,053; 5,217,538; 5,227,005; 5,413,153; 5,558,138; 5,634,500; 5,713,403; 6,276,113; 6,213,169; 6,189,578; 6,192,946; 6,374,575; 6,365,054; 6,619,016; 6,474,368; 6,494,238; 6,470,922; and 6,463,964.

Some examples of control systems which measure operating parameters and learn therefrom that may possibly be utilized or possibly adapted for use in at least one possible embodiment of the present application may possibly be found in the following: U.S. Pat. No. 4,655,188 issued to Tomisawa et al. on Apr. 7, 1987; U.S. Pat. No. 5,191,272 issued to Torii et al. on Mar. 2, 1993; U.S. Pat. No. 5,223,820, issued to Sutterlin et al. on Jun. 29, 1993; and U.S. Pat. No. 5,770,934 issued to Theile on Jun. 23, 1998.

Some examples of computer systems that may possibly be utilized or possibly adapted for use in at least one possible embodiment of the present application may possibly be found in the following: U.S. Pat. No. 5,416,480 issued to Roach et al. on May 16, 1995; U.S. Pat. No. 5,479,355 issued to Hyduke on Dec. 26, 1995; U.S. Pat. No. 5,481,730 issued to Brown et al. on Jan. 2, 1996; U.S. Pat. No. 5,805,094 issued to Roach et al. on Sep. 8, 1998; U.S. Pat. No. 5,881,227 issued to Atkinson et al. on Mar. 9, 1999; and U.S. Pat. No. 6,072,462 issued to Moshovich on Jun. 6, 2000.

Some examples of control valve apparatus that may possibly be utilized or possibly adapted for use in at least one possible embodiment of the present application may possibly be found in the following: U.S. Pat. No. 5,406,975 issued to Nakamichi et al. on Apr. 18, 1995; U.S. Pat. No. 5,503,184 issued to Reinartz et al. on Apr. 2, 1996; U.S. Pat. No. 5,706,849 issued to Uchida et al. on Jan. 13, 1998; U.S. Pat. No. 5,975,115 issued to Schwegler et al. on Nov. 2, 1999; U.S. Pat. No. 6,142,445 issued to Kawaguchi et al. on Nov. 7, 2000; and U.S. Pat. No. 6,145,538 issued to Park on Nov. 14, 2000.

Some examples of electric control valves that may possibly be utilized or possibly adapted for use in at least one possible embodiment of the present application may possibly be found in the following: U.S. Pat. No. 4,431,160 issued to Burt et al. on Feb. 14, 1984; and U.S. Pat. No. 4,609,176 issued to Powers on Sep. 2, 1986.

Some examples of pneumatic arrangements that may possibly be utilized or possibly adapted for use in at least one possible embodiment of the present application may possibly be found in the following: U.S. Pat. No. 6,609,767 issued to Mortenson et al. on Aug. 26, 2003; U.S. Pat. No. 6,632,072 issued to Lipscomb et al. on Oct. 14, 2003; U.S. Pat. No. 6,637,838 issued to Watanabe on Oct. 28, 2003; U.S. Pat. No. 6,659,693 issued to Perkins et al. on Dec. 9, 2003; U.S. Pat. No. 6,668,848 issued to Ladler et al. on Dec. 30, 2003; and U.S. Pat. No. 6,676,229 issued to Marra et al. on Jan. 13, 2004.

Some examples of apparatus and methods of sterilizing or cleaning containers that may possibly be utilized or possibly adapted for use in at least one possible embodiment of the present application may possibly be found in the following: U.S. Pat. No. 5,092,356 issued to Grot on Mar. 3, 1992; U.S. Pat. No. 5,320,144 issued to Ahlers on Jun. 14, 1994; U.S. Pat. No. 5,533,552 issued to Ahlers on Jul. 9, 1996; U.S. Pat. No. 5,558,135 issued to Kronseder et al. on Sep. 24, 1996; and U.S. Pat. No. 5,896,899 issued to Schlitz on Apr. 27, 1999, and in U.S. Publication No. 20060011262, published Jan. 19, 2006, and entitled "Beverage bottling plant for filling bottles with a liquid beverage material having a treatment device for the treatment of bottles."

Some examples of sterilizing or cleaning agents and concentrations thereof that may possibly be utilized or possibly adapted for use in at least one possible embodiment of the present application may possibly be found in the following: U.S. Pat. No. 6,039,922 issued to Swank et al. on Mar. 21, 2000; U.S. Pat. No. 6,244,275 issued to Ziegler et al. on Jun. 12, 2001; U.S. Pat. No. 6,406,666 issued to Cicla et al. on Jun. 18, 2002; and U.S. Pat. No. 6,612,149 issued to Wang et al. on Sep. 2, 2003.

Some examples of nozzle structures that may possibly be utilized or possibly adapted for use in at least one possible embodiment of the present application may possibly be found in the following: U.S. Pat. No. 6,042,026 issued to Buehler, II on Mar. 28, 2000; U.S. Pat. No. 6,394,366 issued to Adams on May 28, 2002; U.S. Pat. No. 6,402,062 issued to Bendig et al. on Jun. 11, 2002; U.S. Pat. No. 6,616,072 issued to Harata et al. on Sep. 9, 2003; U.S. Pat. No. 6,666,386 issued to Huang on Dec. 23, 2003; and U.S. Pat. No. 6,681,498 issued to Steffan on Jan. 27, 2004.

Some examples of heater arrangements that may possibly be utilized or possibly adapted for use in at least one possible embodiment of the present application may possibly be found in the following: U.S. Pat. No. 6,404,421 issued to Meijler et al. on Jun. 11, 2002; U.S. Pat. No. 6,515,264 issued to Toya et al. on Feb. 4, 2003; U.S. Pat. No. 6,548,786 issued to Takizawa et al. on Apr. 15, 2003; U.S. Pat. No. 6,555,796 issued to Cusack on Apr. 29, 2003; U.S. Pat. No. 6,633,727 issued to Henrie et al. on Oct. 14, 2003; and U.S. Pat. No. 6,677,557 issued to Ito et al. on Jan. 13, 2004.

Some examples of filling machines that utilize electronic control devices to control various portions of a filling or bottling process and that may possibly be utilized or possibly adapted for use in at least one possible embodiment of the present application may possibly be found in the following: U.S. Pat. No. 4,821,921 issued to Cartwright et al. on Apr. 18, 1989; U.S. Pat. No. 5,056,511 issued to Ronge on Oct. 15, 1991; U.S. Pat. No. 5,273,082 issued to Paasche et al. on Dec. 28, 1993; and U.S. Pat. No. 5,301,488 issued to Ruhl et al. on Apr. 12, 1994.

Some examples of electric valves which may possibly be utilized or adapted for use in at least one possible embodiment may possibly be found in the following: U.S. Pat. No. 5,941,502, entitled "Electric valve assembly and method of making same;" U.S. Pat. No. 5,161,776, entitled "High speed electric valve;" U.S. Pat. No. 4,770,389, entitled "Electric valve device;" U.S. Pat. No. 4,699,167, entitled "Electric valve;" U.S. Pat. No. 4,681,298, entitled "Slidable electric valve device having a spring;" U.S. Pat. No. 4,580,761, entitled "Electric valve device having a rotatable core;" and U.S. Pat. No. 4,498,491, entitled "Thermo-electric valve."

The following patents, patent applications or patent publications, except for the exceptions indicated herein, are hereby incorporated by reference as if set forth in their entirety herein, as follows: WO 2006/128884 A2, having the title "APPARATUS AND METHODS FOR TREATING COMPONENTS OF PACKAGING UNITS, PARTICULARLY BOTTLES AND/OR CAPS," published on Dec. 7, 2006; DE 36 37 798 A1, having the following English translation of the German title "Pumping and dosing device for gaseous liquids," published on May 11, 1988; DE 38 19 419 A1, having the following English translation of the German title "PROPORTIONING DEVICE FOR ACCURATE AND RELIABLE DOSING," published on Dec. 14, 1989; and U.S. Pat. No. 5,527,507, having the title "Accumulator based liquid metering system and method," published on Jun. 18, 1996.

All of the patents, patent applications or patent publications, except for the exceptions indicated herein, which were cited in the International Search Report, dated Jun. 24, 2009, and/or cited elsewhere are hereby incorporated by reference as if set forth in their entirety herein, as follows: DE 40 36 950, having the following English translation of the German title "Supplying sterilising liq. to packing containers—involves through-flow measuring instrument and degasification device to remove bubbles," published on May 21, 1992; DE 199 56 186, having the following English translation of the German title "Packaging container sterilization process, comprises using a mixing nozzle to produce a disinfectant—steam mixt which is then sprayed onto the container surfaces," published on May 23, 2001; and DE 36 37 798, having the following English translation of the German title "Pumping and dosing device for gaseous liquids," published on May 11, 1988.

All of the patents, patent applications or patent publications, except for the exceptions indicated herein, which were cited in the German Office Action dated Jun. 12, 2008, and/or cited elsewhere are hereby incorporated by reference as if set forth in their entirety herein, as follows: DE 37 19 419, having the following English translation of the German title "PROPORTIONING DEVICE FOR ACCURATE AND RELIABLE DOSING," published on Dec. 14, 1989; DE 36 37 789, having the following English translation of the German title "Pumping and dosing device for gaseous liquids," published on May 11, 1988; EP 0 353 486, having the title "Dosage device particularly for dosing sterilizing substances used in the sterilization treatment of bottles, containers and the like," published on Feb. 7, 1990; U.S. Pat. No. 5,527,507, having the title "Accumulator based liquid metering system and method," published on Jun. 18, 1996; and WO 2006/128884, having the title "APPARATUS AND METHODS FOR TREATING COMPONENTS OF PACKAGING UNITS, PARTICULARLY BOTTLES AND/OR CAPS," published on Dec. 7, 2006.

The patents, patent applications, and patent publications listed above in the preceding paragraphs are herein incorporated by reference as if set forth in their entirety. The purpose of incorporating U.S. patents, foreign patents, publications, etc. is solely to provide additional information relating to technical features of one or more embodiments, which information may not be completely disclosed in the wording in the pages of this application. However, words relating to the opinions and judgments of the author and not directly relating to the technical details of the description of the embodiments therein are not incorporated by reference. The words all, always, absolutely, consistently, preferably, guarantee, particularly, constantly, ensure, necessarily, immediately, endlessly, avoid, exactly, continually, expediently, ideal, need, must, only, perpetual, precise, perfect, require, requisite, simultaneous, total, unavoidable, and unnecessary, or words substantially equivalent to the above-mentioned words in this sentence, when not used to describe technical features of one or more embodiments of the patents, patent applications, and patent publications, are not considered to be incorporated by reference herein.

The corresponding foreign and international patent publication applications, namely, Federal Republic of Germany Patent Application No. 10 2007 039 010.8, filed on Aug. 17, 2007, having inventors Thomas HEROLD and Roland TOPF, and DE-OS 10 2007 039 010.8 and DE-PS 10 2007 039 010.8, and International Application No. PCT/EP2008/005828, filed on Jul. 17, 2008, having WIPO Publication No. WO 2009/042418 and inventors Thomas HEROLD and Roland TOPF, are hereby incorporated by reference as if set forth in their entirety herein for the purpose of correcting and explaining any possible misinterpretations of the English translation thereof. In addition, the published equivalents of the above corresponding foreign and international patent publication applications, and other equivalents or corresponding applications, if any, in corresponding cases in the Federal Republic of Germany and elsewhere, and the references and documents cited in any of the documents cited herein, such as the patents, patent applications and publications, are hereby incorporated by reference as if set forth in their entirety herein.

The purpose of incorporating the corresponding foreign equivalent patent application(s), that is, PCT/EP2008/005828 and German Patent Application 10 2007 039 010.8, is solely for the purpose of providing a basis of correction of any wording in the pages of the present application, which may have been mistranslated or misinterpreted by the translator. However, words relating to opinions and judgments of the author and not directly relating to the technical details of the description of the embodiments therein are not to be incorporated by reference. The words all, always, absolutely, consistently, preferably, guarantee, particularly, constantly, ensure, necessarily, immediately, endlessly, avoid, exactly, continually, expediently, ideal, need, must, only, perpetual, precise, perfect, require, requisite, simultaneous, total, unavoidable, and unnecessary, or words substantially equivalent to the above-mentioned word in this sentence, when not used to describe technical features of one or more embodiments of the patents, patent applications, and patent publications, are not generally considered to be incorporated by reference herein.

Statements made in the original foreign patent applications PCT/EP2008/005828 and DE 10 2007 039 010.8 from which this patent application claims priority which do not have to do with the correction of the translation in this patent application are not to be included in this patent application in the incorporation by reference.

Any statements about admissions of prior art in the original foreign patent applications PCT/EP2008/005828 and DE 10 2007 039 010.8 are not to be included in this patent application in the incorporation by reference, since the laws relating to prior art in non-U.S. Patent Offices and courts may be substantially different from the Patent Laws of the United States.

U.S. application Ser. No. 12/707,431, entitled "A CONTAINER FILLING PLANT, SUCH AS A BOTTLE OR CAN FILLING PLANT, HAVING EQUIPMENT FOR TREATING CONTAINERS AND A METHOD OF OPERATING SUCH EQUIPMENT," filed on Feb. 17, 2010, having inventors Daryoush SANGI and Thomas HEROLD, and the foreign applications corresponding thereto, specifically German Application DE 10 2007 039 008.6, filed Aug. 17, 2007, and International Application PCT/EP2008/006116, filed Jul. 25, 2008, and published on Feb. 26, 2009 as WO2009/024247, are hereby incorporated by reference, except for the exceptions indicated herein, as if set forth in their entirety herein.

All of the references and documents, cited in any of the documents cited herein, are hereby incorporated by reference as if set forth in their entirety herein. All of the documents cited herein, referred to in the immediately preceding sentence, include all of the patents, patent applications and publications cited anywhere in the present application.

The description of the embodiment or embodiments is believed, at the time of the filing of this patent application, to adequately describe the embodiment or embodiments of this patent application. However, portions of the description of the embodiment or embodiments may not be completely applicable to the claims as originally filed in this patent application, as amended during prosecution of this patent application, and as ultimately allowed in any patent issuing from this patent application. Therefore, any statements made relating to the embodiment or embodiments are not intended to limit the claims in any manner and should not be interpreted as limiting the claims in any manner.

The details in the patents, patent applications and publications may be considered to be incorporable, at applicant's option, into the claims during prosecution as further limitations in the claims to patentably distinguish any amended claims from any applied prior art.

The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the embodiment or embodiments, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

The abstract of the disclosure is submitted herewith as required by 37 C.F.R. §1.72(b). As stated in 37 C.F.R. §1.72(b):

A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims. Therefore, any statements made relating to the abstract are not intended to limit the claims in any manner and should not be interpreted as limiting the claims in any manner.

The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

AT LEAST PARTIAL NOMENCLATURE

1 Device
2 Bottle
3 Rotor
4 Inlet
5 Outlet
6 Treatment head
6.1 Mixing chamber
6.2 Evaporator
6.1.1 Connection for sterile air with mixing head nozzle
6.1.2 Connection for hydrogen peroxide with mixing head nozzle
7 Bottle or container carrier
8 Tube
9, 9a Metering and supplying system
10, 10a Ring line
11, 11a Flow meter
12 Filter
13, 13a Metering valve
14, 14a Storage or supplying container for hydrogen peroxide
15 Collecting container
16 Line
17 Pump
18 Non return valve
19, 20 Level switch
21 Supply line
22 Control valve
23, 24 Level switch
25 Supply line
26 Control valve
27 Electronic control device
28, 28a Throttle
29 Pump
30 Filter
31 Gas separator
A Direction of flow of hydrogen peroxide in ring channel 10
B Direction of flow of hydrogen peroxide in ring channel 10a
$N_{14}$, $N_{15}$ Level

What is claimed is:

1. A $H_2O_2$ supply arrangement comprising:
a $H_2O_2$ storage container;
a pressurized line arrangement configured to cycle $H_2O_2$ out from said $H_2O_2$ storage container and back into said $H_2O_2$ storage container;
a plurality of metering valves, each comprising an openable and closable exit configured to control flow of doses of $H_2O_2$ from the $H_2O_2$ being cycled in said line arrangement to a corresponding article sterilization device; and
each of said exits is configured to be closed such that only cycled flow of $H_2O_2$ through said line arrangement is permitted, and to be opened such that both cycled flow of $H_2O_2$ through said line arrangement and flow of $H_2O_2$ through said exits are permitted.

2. The $H_2O_2$ supply arrangement according to claim 1, wherein said line arrangement comprises at least one line having a cross-section sufficiently large to minimize pressure losses and/or pressure fluctuations and/or changes in volume flow resulting from opening and closing of said metering valves, and sufficiently large to promote a substantially identical or constant pressure at each of said metering valves.

3. The $H_2O_2$ supply arrangement according to claim 2, wherein said line arrangement is configured such that the flow resistance for said $H_2O_2$ flowing through each of said metering valves upon said exit being closed is substantially identical or identical to the flow resistance upon said exit being opened.

4. The $H_2O_2$ supply arrangement according to claim 3, wherein said storage container is configured to generate pressure at said metering valves, and comprises the sole source of pressure at said metering valves.

5. The $H_2O_2$ supply arrangement according to claim 4, wherein said $H_2O_2$ supply arrangement comprises a collecting container configured to collect $H_2O_2$ returned via said line arrangement, which collecting container is connected to said $H_2O_2$ storage container by a connecting line.

6. The $H_2O_2$ supply arrangement according to claim 5, wherein:
each of said metering valves is configured to meter doses of $H_2O_2$ from said line arrangement to a mixing arrangement which is configured to mix a gaseous or vaporous carrier medium with doses of $H_2O_2$ from said metering valve;
the pressure in said collecting container is less than the pressure at said metering valves; and
said connecting line comprises a pump being configured and disposed to pump $H_2O_2$ from said collecting container to said storage container.

7. The $H_2O_2$ supply arrangement according to claim 6, wherein:
at least one of said storage container and said collecting container comprises a gas space being configured and disposed to permit discharge of gaseous decomposition products of said $H_2O_2$;
said line arrangement comprises gas separators being configured and disposed to separate or discharge gaseous decomposition products of said $H_2O_2$; and
one of (A) and (B):
(A) said line arrangement comprises a plurality of lines configured to be connected to a plurality of article sterilization devices, wherein each line is configured to be connected to at least one of the article sterilization devices; and
(B) said line arrangement comprises a single line configured to be connected to all article sterilization devices.

8. The $H_2O_2$ supply arrangement according to claim 7, in combination with a plurality of article sterilization devices disposed on the periphery of a rotor and configured to sterilize articles comprising bottles or containers.

9. The $H_2O_2$ supply arrangement according to claim 3, wherein:
said line arrangement comprises at least one pump configured to generate pressure at said metering valves;
said storage container is configured to provide a gas space above $H_2O_2$ in said storage container; and said line arrangement comprises gas separators being configured and disposed to separate or discharge gaseous decomposition products of $H_2O_2$ in said line arrangement.

10. The $H_2O_2$ supply arrangement according to claim 1, further comprising a computer control device configured to repeatedly switch open and closed said exits to substantially immediately allow flow of $H_2O_2$ out of said exits, and to substantially immediately stop flow of $H_2O_2$ out of said exits, to thereby meter doses of $H_2O_2$ from said line arrangement to a plurality of article sterilization devices.

11. A $H_2O_2$ supply arrangement comprising:
a $H_2O_2$ storage container;
a pressurized line arrangement configured to cycle $H_2O_2$ out from said $H_2O_2$ storage container and back into said $H_2O_2$ storage container;
a plurality of metering valves, each comprising an openable and closable exit configured to control flow of doses of $H_2O_2$ from the $H_2O_2$ being cycled in said line arrangement to a corresponding article sterilization device; and
said storage container is pressurized to generate pressure at said metering valves, and comprises the sole source of pressure at said metering valves.

12. A $H_2O_2$ supply arrangement comprising:
a $H_2O_2$ storage container;
a pressurized line arrangement configured to cycle $H_2O_2$ out from said $H_2O_2$ storage container and back into said $H_2O_2$ storage container;
a plurality of metering valves, each comprising an openable and closable exit configured to control flow of doses of $H_2O_2$ from the $H_2O_2$ being cycled in said line arrangement to a corresponding article sterilization device; and
a collecting container configured to collect $H_2O_2$ returned via said line arrangement, which collecting container is connected to said $H_2O_2$ storage container by a connecting line.

13. A method of supplying $H_2O_2$ comprising:
cycling $H_2O_2$ via a pressurized line arrangement out from a $H_2O_2$ storage container and back into said $H_2O_2$ storage container;
opening and closing an exit in each of a plurality of metering valves and thereby metering doses of $H_2O_2$ from the $H_2O_2$ being cycled in said line arrangement to a plurality of article sterilization devices; and
pressurizing said storage container and generating a pressure at said metering valves solely with pressure from within said storage container.

14. The method of supplying $H_2O_2$ according to claim 13, wherein said step of metering comprises using a computer control device to repeatedly switch open and closed at least one of said exits to substantially immediately allow flow of $H_2O_2$ out of at least one of said exits, and to substantially immediately stop flow of $H_2O_2$ out of at least one of said exits.

15. The method of supplying $H_2O_2$ according to claim 13, wherein said method further comprises maintaining substantially the same pressure throughout said line arrangement and at said metering valves, and thereby minimizing disturbance of $H_2O_2$ and decomposition of $H_2O_2$ caused by such disturbance.

16. The method of supplying $H_2O_2$ according to claim 13, wherein said method further comprises:
rotating a rotor, about the periphery of which said plurality of article sterilization devices are mounted;
supplying articles to be sterilized to said rotor; and
sterilizing said articles while said articles are moved by said rotor.

17. A method of supplying $H_2O_2$ comprising continuously and uninterruptedly cycling $H_2O_2$ via a pressurized line arrangement out from a $H_2O_2$ storage container and back into said $H_2O_2$ storage container, while opening and closing an exit in each of a plurality of metering valves and thereby metering doses of $H_2O_2$ from the $H_2O_2$ being cycled in said line arrangement to a plurality of article sterilization devices.

* * * * *